(12) United States Patent
Lim et al.

(10) Patent No.: US 11,309,627 B2
(45) Date of Patent: Apr. 19, 2022

(54) WIRELESS CHARGING LOOP ANTENNA

(71) Applicant: XI'AN JIAOTONG-LIVERPOOL UNIVERSITY, Jiangsu (CN)

(72) Inventors: Eng Gee Lim, Jiangsu (CN); Jingchen Wang, Jiangsu (CN); Zhao Wang, Jiangsu (CN); Mark Paul Leach, Jiangsu (CN); Yi Huang, Jiangsu (CN)

(73) Assignee: XI'AN JIAOTONG-LIVERPOOL UNIVERSITY, Jiangsu (CN)

( * ) Notice: Subject to any disclaimer, the term of this patent is extended or adjusted under 35 U.S.C. 154(b) by 0 days.

(21) Appl. No.: 17/419,291

(22) PCT Filed: Jan. 2, 2020

(86) PCT No.: PCT/CN2020/070045
§ 371 (c)(1),
(2) Date: Jun. 29, 2021

(87) PCT Pub. No.: WO2020/140928
PCT Pub. Date: Jul. 9, 2020

(65) Prior Publication Data
US 2022/0045421 A1    Feb. 10, 2022

(30) Foreign Application Priority Data
Jan. 3, 2019    (CN) .......................... 201910003407.2

(51) Int. Cl.
*H02J 7/00* (2006.01)
*H01Q 1/38* (2006.01)
(Continued)

(52) U.S. Cl.
CPC ............ *H01Q 1/38* (2013.01); *A61N 1/3787* (2013.01); *H01Q 7/00* (2013.01); *H01Q 21/06* (2013.01); *H02J 50/27* (2016.02)

(58) Field of Classification Search
None
See application file for complete search history.

(56) References Cited

U.S. PATENT DOCUMENTS 7,191,013 B1 * 3/2007 Miranda .............. H01Q 1/2216
607/60
9,531,075 B2 * 12/2016 Werner .................. H01Q 9/045
(Continued)

FOREIGN PATENT DOCUMENTS

CN    107273250 A    10/2017
CN    107276250 A    10/2017
(Continued)

OTHER PUBLICATIONS

Song, Young (Study and Optimizing Design of Wireless Charing System for Implantable Medical Equipment (Sep. 30, 2018).
(Continued)

*Primary Examiner* — Arun C Williams

(57) ABSTRACT

Provided is a wireless charging loop antenna. The wireless charging loop antenna includes an extracorporal planar loop antenna and an intracorporal planar loop antenna. The intracorporal planar loop antenna is disposed inside a body, and the extracorporal planar loop antenna is disposed on a skin outside the body. The extracorporal planar loop antenna includes an extracorporal antenna substrate, an extracorporal loop radiation patch, paired connection radiation patches and a patch capacitor. The extracorporal loop radiation patch is provided with at least one extracorporal radiation patch gap. The patch capacitor is disposed at one of the at least one extracorporal radiation patch gap. The extracorporal loop radiation patch and the paired connection radiation patches form a circuit. The extracorporal loop radiation patch, the paired connection radiation patches and the patch capacitor are all on a same surface of the extracorporal antenna substrate.

7 Claims, 5 Drawing Sheets

(51) Int. Cl.
*H01Q 7/00* (2006.01)
*A61N 1/378* (2006.01)
*H02J 50/27* (2016.01)
*H01Q 21/06* (2006.01)

(56) References Cited

U.S. PATENT DOCUMENTS

| | | | |
|---|---|---|---|
| 2013/0181874 A1* | 7/2013 | Park | H01Q 9/42 |
| | | | 343/718 |
| 2017/0203109 A1 | 7/2017 | Maile et al. | |
| 2018/0323511 A1* | 11/2018 | Urzhumov | H01Q 1/2225 |
| 2019/0058247 A1* | 2/2019 | Matlin | H01Q 1/002 |
| 2021/0098865 A1* | 4/2021 | Morgan | H01Q 1/273 |

FOREIGN PATENT DOCUMENTS

| | | |
|---|---|---|
| CN | 107332320 A | 11/2017 |
| CN | 109638444 A | 4/2019 |

OTHER PUBLICATIONS

Lu, Yao et al., "A Wireless Charging Circuit with High Power Efficiency and Security for Implantable Devices", 2016 IEEE BioCAS (Jan. 26, 2017).
ISR for PCT/CN2020/070045 (Mar. 27, 2020).

* cited by examiner

WIRELESS CHARGING LOOP ANTENNA

CROSS-REFERENCE TO RELATED APPLICATION

This is a National stage application, filed under 37 U.S.C. 371, of International Patent Application NO. PCT/CN2020/070045, filed on Jan. 2, 2020, which is based on and claims priority to Chinese Patent Application No. 201910003407.2 filed Jan. 3, 2019 with the CNIPA, the disclosure of which is incorporated herein by reference in its entirety.

TECHNICAL FIELD

The present disclosure relates to a wireless charging antenna, such as a wireless charging loop antenna applied to an implantable cardiac pacemaker.

BACKGROUND

In October 1958, Hospital Karolinska in Sweden completed the world's first implantation of the implantable artificial cardiac pacemaker. The operation was carried out by a surgeon, Professor Ake Senming. The implanted cardiac pacemaker was of fixed frequency type and designed by Dr. Rune Elmqvist of Elema-Schnander Company. The pacemaker is circular in shape and is powered by two nickel-cadmium batteries connected in series. The pacemaker needs to be charged once a week through extracorporal induction. Patient Arne Larsson had completed atrioventricular block, and suffered from the frequent occurrence of Adam-stoke syndrome caused by cardiac arrest. The effect of drug therapy is not good. The patient has lived and worked with the cardiac pacemakers for 46 years since the age of 40, and died of cancer at the age of 86. During his life, he replaced 26 pacemakers.

The artificial cardiac, as an implantable medical device, realizes the function of pumping blood by assisting or replacing the weak heart, and is an irreplaceable treatment means. The application of the implantable cardiac pacemaker and the development of the technology of the implantable cardiac pacemaker are of revolutionary significance for the treatment of bradyarrhythmia. As a first clinical therapy that can effectively regulate the patient's heart rhythm or rate and further improve the myocardial contraction, the implantable cardiac pacemaker greatly improves the clinical prognosis of patients suffering from sinus node dysfunction and severe atrioventricular block. With the continuous deepening of understanding of pacing hemodynamics and the further development of pacemaker technology, the pacemakers are not only used for the treatment of symptomatic bradycardia, but also expanded to the treatment of diseases based on hemodynamic changes, and indications of the pacemakers are continuously expanding.

With the progress and development of electronic industry, great progress has been made in the pulse generator which is the main component of the cardiac pacemaker. The application of large-area integrated circuits, ultra-small components and chips enables the pacemaker to develop towards being small, light, thin and reliable. In the related art, the smallest cardiac pacemaker has a long radius less than 6 cm and the lightest cardiac pacemaker weighs less than 20 g. However, in terms of energy use, although the cardiac pacemaker in the related art uses the lithium iodine battery with a service life up to 12 years, the implantation surgery still needs to be performed for implanting a new cardiac pacemaker to maintain the normal life. The battery plays a much more important role as a power supply system of the implantable medical equipment (such as the cardiac pacemaker), but the volume and life of the battery limit the development of the implantable medical equipment. The implantable medical equipment in a wireless energy transmission type can not only avoid the pain and inconvenience brought to patients by the conventional implantable equipment in a wire connection type or a battery type, but also can be widely applied to the medical industry. Therefore, the current and future development directions for the implantable medical equipment are having a longer service lifetime, a more stable current output and rechargeable power supply without replacement, reducing the family burden of the patients and bringing good news to the patients.

In the related art, the wireless energy transmission technologies applied to the implantable medical equipment include electromagnetic induction, magnetic coupled resonance and capacitive coupling. These technologies have their own advantages and disadvantages, and the main problems are short transmission distance and low transmission efficiency.

SUMMARY

The present disclosure provides a planar loop antenna which is applied to a cardiac pacemaker, can carry out wireless energy transmission, and has a small volume and high energy transmission efficiency.

The technical solutions of the present disclosure are as follows.

A wireless charging loop antenna, applied to an implantable cardiac pacemaker, includes: an extracorporal planar loop antenna and an intracorporal planar loop antenna. The intracorporal planar loop antenna is disposed inside a body, and the extracorporal planar loop antenna is disposed, outside the body; the extracorporal planar loop antenna includes an extracorporal antenna substrate, an extracorporal loop radiation patch, paired connection radiation patches and a patch capacitor; the extracorporal loop radiation patch and the paired connection radiation patches form a circuit; the extracorporal loop radiation patch, the paired connection radiation patches and the patch capacitor are all on a same surface of the extracorporal antenna substrate; the extracorporal loop radiation patch is provided with at least one extracorporal radiation patch gap; the extracorporal radiation patch includes a first loop radiation patch, a second loop radiation patch, a third loop radiation patch and a fourth loop radiation patch; the second loop radiation patch is disposed outside a ring of the first loop radiation patch, the third loop radiation patch is disposed outside a ring of the second loop radiation patch, and the fourth loop radiation patch is disposed outside a ring of the third loop radiation patch; the patch capacitor is disposed at one of the at least one extracorporal radiation patch gap; the paired connection radiation patches include: a first pair of connection radiation patches, a second pair of connection radiation patches and a third pair of connection radiation patches; the first pair of connection radiation patches connects the first loop radiation patch to the second loop radiation patch; the second pair of connection radiation patches connects the second loop radiation patch to the third loop radiation patch; and the third pair of connection radiation patches connects the third loop radiation patch to the fourth loop radiation patch.

In an embodiment, the intracorporal planar loop antenna includes an intracorporal antenna substrate and an intracorporal loop radiation patch; the intracorporal loop radiation patch is disposed on the intracorporal antenna substrate; and the intracorporal loop radiation patch is provided with an intracorporal radiation patch gap.

BRIEF DESCRIPTION OF DRAWINGS

This disclosure is further described below with reference to the drawings and embodiments.

REFERENCE LIST

Figure 1:
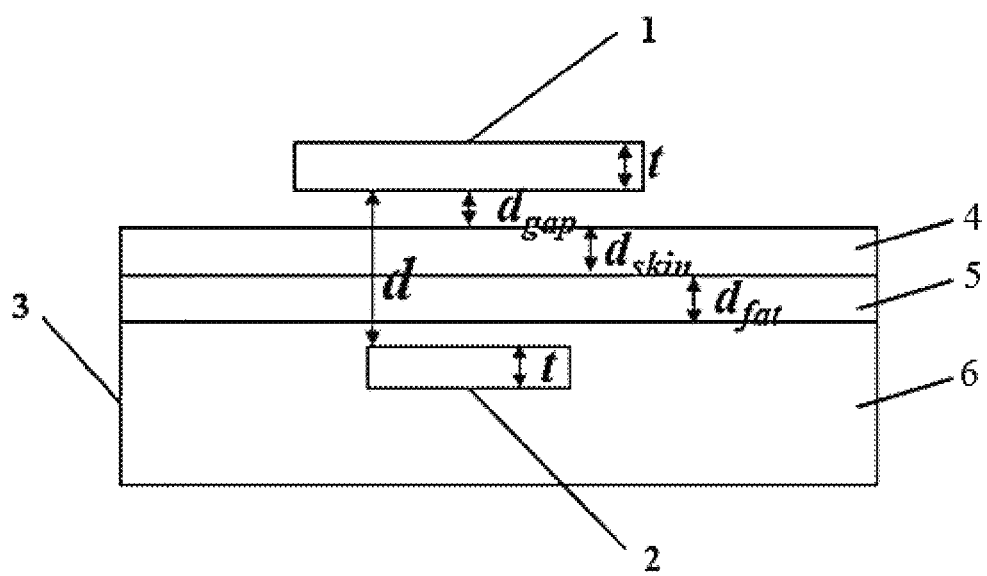
FIG. 1 is an assembly diagram of a wireless charging loop antenna applied to an implantable cardiac pacemaker according to the present case.

1 Extracorporal planar loop antenna
2 Intracorporal planar loop antenna
3 Local human body model
4 Skin
5 Fat
6 Muscle
11 Extracorporal antenna substrate
12 Patch capacitor
13 Extracorporal radiation patch gap
14 First loop radiation patch
15 Second loop radiation patch
16 Third loop radiation patch
17 Fourth loop radiation patch
18 First pair of connection radiation patches
19 Second pair of connection radiation patches
110 Third pair of connection radiation patches
21 Intracorporal antenna substrate
22 Intracorporal loop radiation patch
23 Intracorporal radiation patch gap

DETAILED DESCRIPTION

Embodiment

Figure 2:
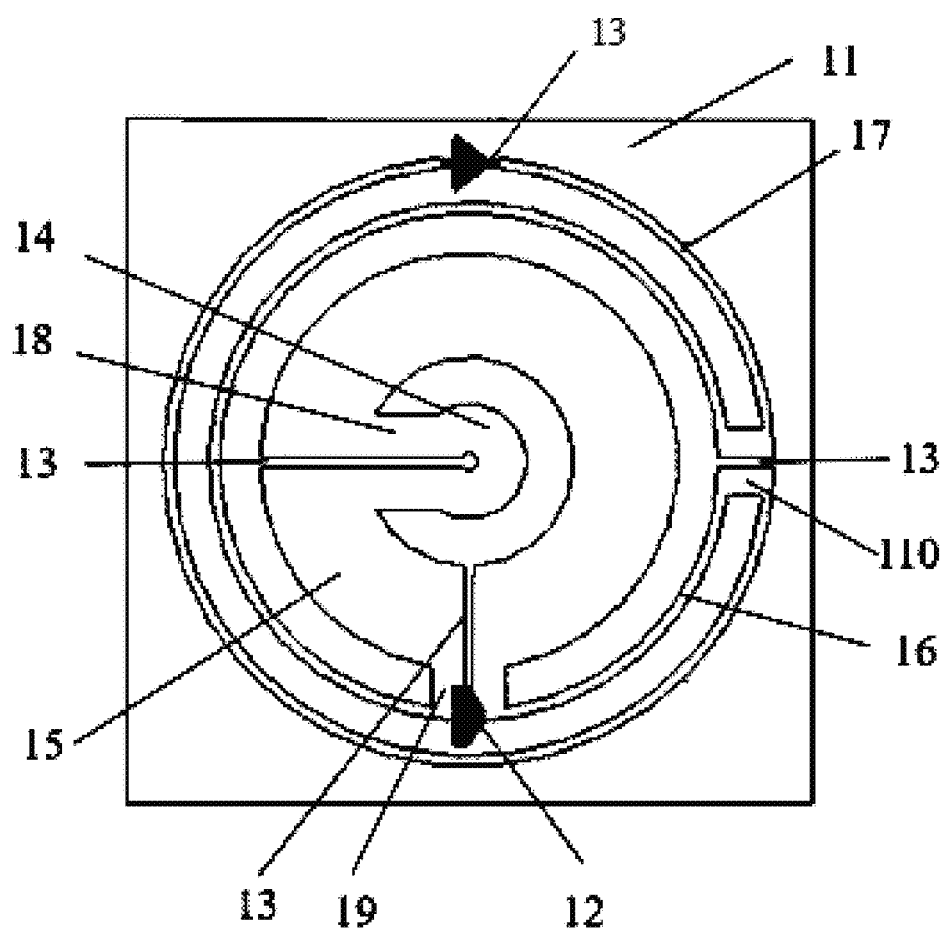
FIG. 2 is a structure diagram of an extracorporal planar loop antenna of the wireless charging loop antenna applied to an implantable cardiac pacemaker according to the present case.
Figure 3:
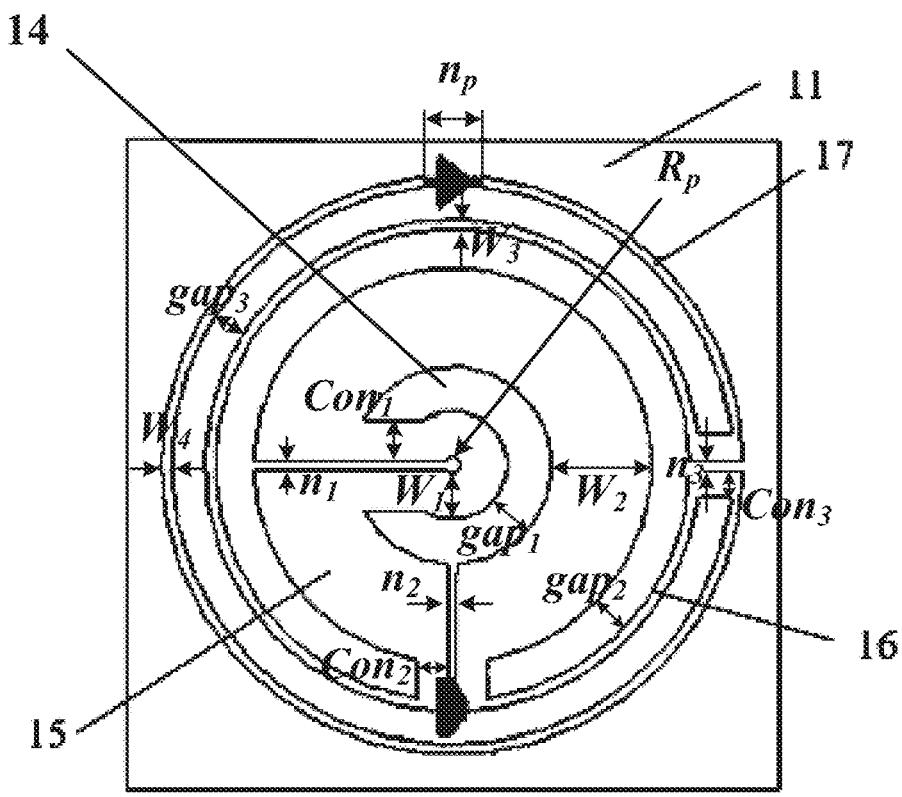
FIG. 3 is a schematic diagram showing size marking of the extracorporal planar loop antenna of the wireless charging loop antenna applied to an implantable cardiac pacemaker according to the present case.
Figure 4:
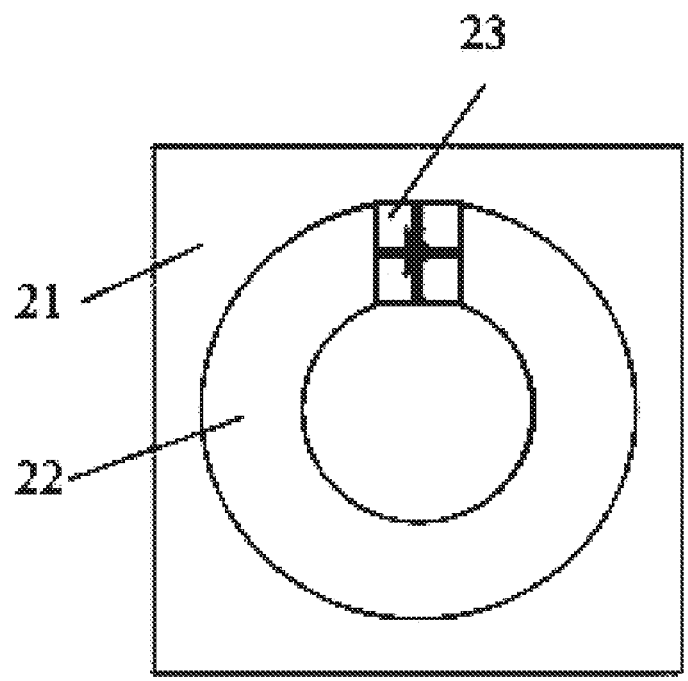
FIG. 4 is a structure diagram of an intracorporal planar loop antenna of the wireless charging loop antenna applied to an implantable cardiac pacemaker according to the present case.

As shown in FIGS. 1-2, a wireless charging loop antenna, applied to an implantable cardiac pacemaker, includes an extracorporal planar loop antenna 1 and an intracorporal planar loop antenna 2. The intracorporal planar loop antenna 2 is disposed inside a body, and the extracorporal planar loop antenna 1 is disposed on a skin outside the body. The extracorporal planar loop antenna 1 includes an extracorporal antenna substrate 11, an extracorporal loop radiation patch, paired connection radiation patches and a patch capacitor 12. The extracorporal loop radiation patch is disposed on the extracorporal antenna substrate 11, the extracorporal loop radiation patch is provided with at least one extracorporal radiation patch gap 13, and the patch capacitor 12 is disposed at one of the at least one extracorporal radiation patch gap 13. The extracorporal loop radiation patch includes a first loop radiation patch 14, a second loop radiation patch 15, a third loop radiation patch 16 and a fourth loop radiation patch 17. The paired connection radiation patches include a first pair of connection radiation patches 18, a second pair of connection radiation patches 19 and a third pair of connection radiation patches 110. The second loop radiation patch 15 is disposed outside a ring of the first loop radiation patch 14, and the first pair of connection radiation patches 18 connects the first loop radiation patch 14 to the second loop radiation patch 15. The third loop radiation patch 16 is disposed outside a ring of the second loop radiation patch 15, and the second pair of connection radiation patches 19 connects the second loop radiation patch 15 to the third loop radiation patch 16. The fourth loop radiation patch 17 is disposed outside a ring of the third loop radiation patch 16, and the third pair of connection radiation patches 110 connects the third loop radiation patch 16 to the fourth loop radiation patch 17. The extracorporal loop radiation patch and the paired connection radiation patches form a circuit, and the extracorporal loop radiation patch, the paired connection radiation patches and the patch capacitor 12 are all on a same surface of the extracorporal antenna substrate 11. The patch capacitor 12 is disposed at an extracorporal radiation patch gap 13 of the first loop radiation patch 14, or at an extracorporal radiation patch gap 13 of the second loop radiation patch 15, or at an extracorporal radiation patch gap 13 of the third loop radiation patch 16, or at an extracorporal radiation patch gap 13 of the fourth loop radiation patch 17. The extracorporal radiation patch gap 13 is disposed at any angle of 0 to 360° of the extracorporal loop radiation patch, and an extracorporal feed point points from one end of the extracorporal radiation patch gap 13 of the fourth loop radiation patch 17 to the other end of the extracorporal radiation patch gap 13 of the fourth loop radiation patch 17.

The intracorporal planar loop antenna 2 includes an intracorporal antenna substrate 21 and an intracorporal loop radiation patch 22. The intracorporal loop radiation patch 22 is disposed on the intracorporal antenna substrate 21, and the intracorporal loop radiation patch 22 is provided with an intracorporal radiation patch gap 23. The intracorporal radiation patch gap 23 is broken at any angle of 0 to 360° of the intracorporal loop radiation patch. An intracorporal feed point points from one end of the intracorporal radiation patch gap 23 to the other end of the intracorporal radiation patch gap 23.

The extracorporal antenna substrate 11 is made of polytetrafluoroethylene, glass fiber reinforced polytetrafluoroethylene, glass-epoxy resin or the like, and has a thickness of 0.25 mm to 1.5 mm, a length of 5 mm to 90 mm and a width of 5 mm to 90 mm. The first loop radiation patch 14 has an inner radius of 0.5 mm to 5 mm and an outer radius of 1 mm to 10 mm. The second loop radiation patch 15 has an inner radius of 1.5 mm to 15 mm and an outer radius of 2 mm to 20 mm. The third loop radiation patch 16 has an inner radius of 2.5 mm to 25 mm, and an outer radius of 3 mm to 30 mm. The fourth annular radiation patch 17 has an inner radius of 3.5 mm to 35 mm and an outer radius of 4 mm to 40 mm. The extracorpoal radiation patch gap 13 has a width of 0.3 mm to 5 mm. The paired connection radiation patches have a length of 0.5 mm to 15 mm and a width of 0.4 mm to 5 mm. A capacitance value of the patch capacitor 12 is 1 pF to 50 pF. The intracorporal antenna substrate 21 is made of polytetrafluoroethylene, glass fiber reinforced polytetrafluoroethylene, glass fiber epoxy resin or the like, and has a thickness of 0.25 mm to 1.5 mm, a length of 5 mm to 50 mm, and a width of 5 mm to 50 mm. The intracorporal loop radiation patch 22 has an inner radius of 0.5 mm to 10 mm and an outer radius of 1 mm to 20 mm. The intracorporal radiation patch gap 23 has a width of 0.5 mm to 5 mm.

In this embodiment, the detailed dimension data and labels are shown in Table 1. The extracorporal antenna substrate 11 is made of glass fiber epoxy resin having an electrical constant of 4.3, a thickness of 1.5 mm, a length of 40 mm and a width of 40 mm, and the first loop radiation patch 14 has an inner radius of 0.5 mm and an outer radius of 3.34 mm. The second loop radiation patch 15 has an inner radius of 6.06 mm and an outer radius of 12.09 mm. The third loop radiation patch 16 has an inner radius of 14.44 mm and an outer radius of 15.08 mm. The fourth loop radiating patch 17 has an inner radius of 17.1 mm and an outer radius of 17.7 mm. The first pair of connection radiation patches 18 has a length of 2.75 mm and a width of 2.47 mm. The second pair of connection radiation patches 19 has a length of 2.36 mm and a width of 1.91 mm. The third pair of connection radiation patches 110 has a length of 2.2 mm and a width of 1.67 mm. The patch capacitor 12 may be placed at a common extracorporal radiation patch gap 13 of the second loop radiation patch 15 and the third loop radiation patch 16. The extracorporal radiation patch gap 13 of the first loop radiation patch 14 has a width of 0.57 mm, the extracorporal radiation patch gap 13 of the second loop radiation patch 15 has a width of 0.5 mm, the extracorporal radiation patch gap 13 of the third loop radiation patch 16 has a width of 0.64 mm and the extracorporal radiation patch gap 13 of the fourth loop radiation patch 17 is 3.4 mm. The capacitance value of the patch capacitor 12 is 7.9 pF. The intracorporal antenna substrate 21 is made of glass fiber epoxy resin material having a dielectric constant of 4.3, and has a thickness of 1.5 mm, a length of 25.5 mm and a width of 25.5 mm. The intracorporal loop radiation patch 22 has an inner radius of 5.56 mm and an outer radius of 10.23 mm. The intracorporal radiation patch gap 23 has a width of 4.1 mm.

Figure 5:
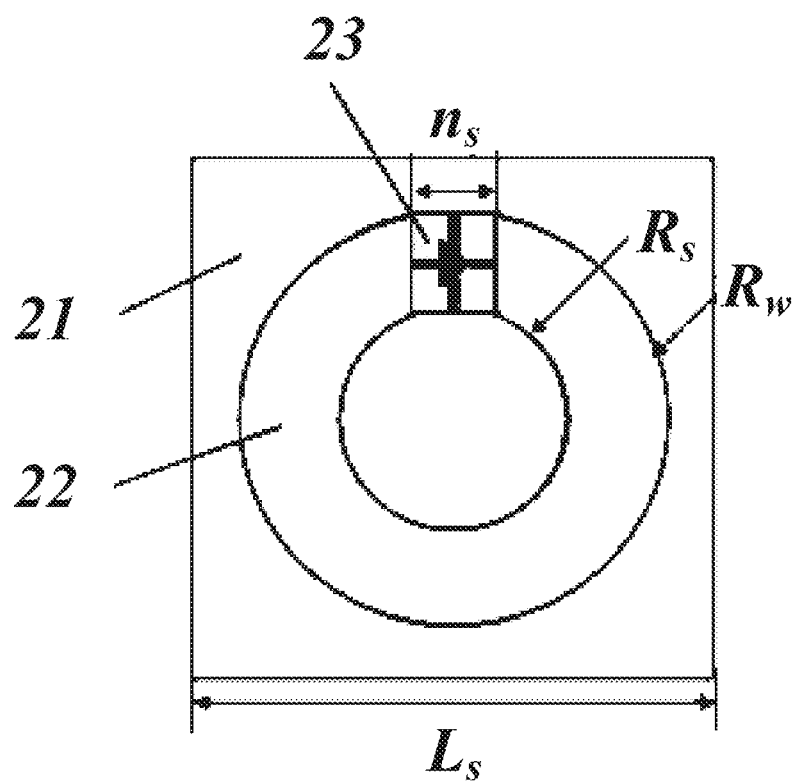
FIG. 5 is a schematic diagram showing size marking of the intracorporal planar loop antenna of the wireless charging loop antenna applied to an implantable cardiac pacemaker according to the present case.
Figure 6:
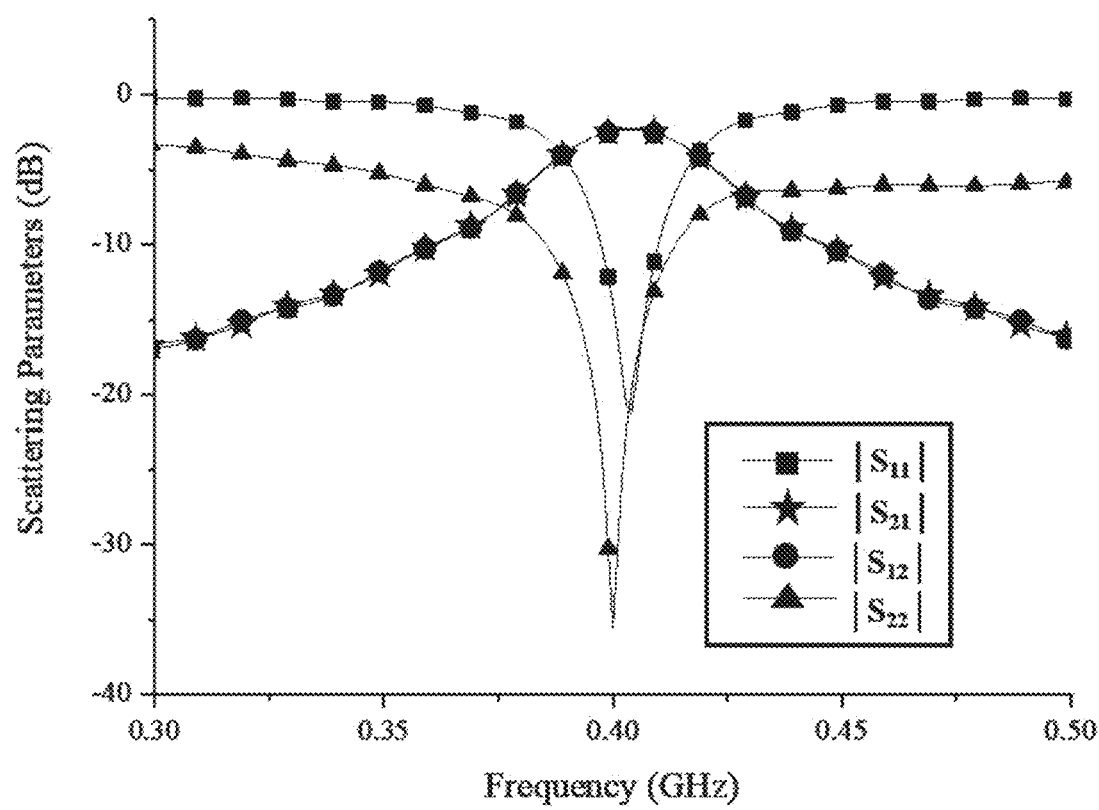
FIG. 6 is a return loss curve of the extracorporal planar loop antenna of the wireless charging loop antenna applied to an implantable cardiac pacemaker according to the present case.
Figure 7:
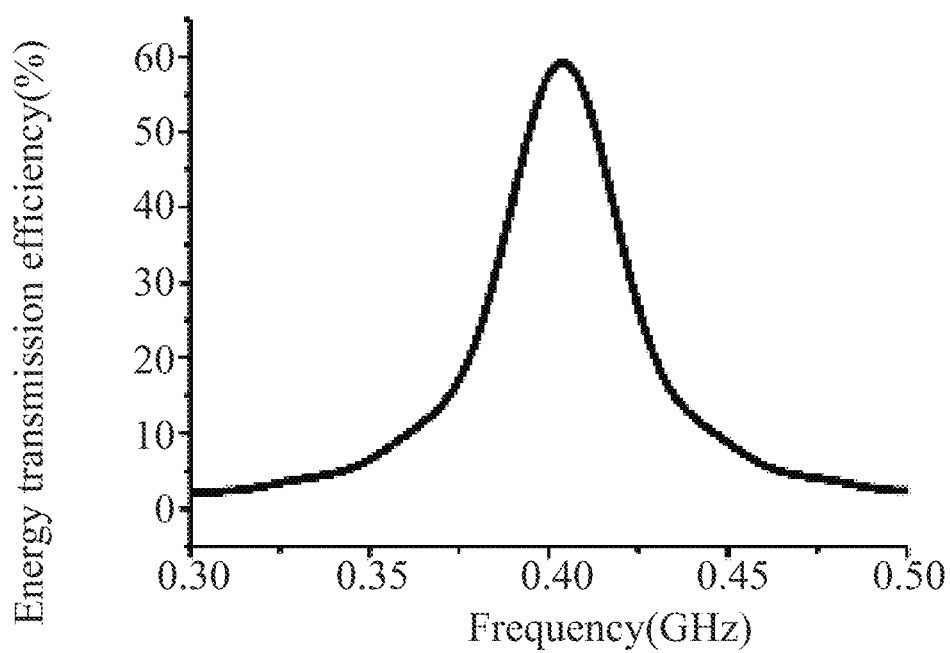
FIG. 7 is an efficiency curve of wireless energy transmission between the extracorporal planar loop antenna and the intracorporal planar loop antenna of the wireless charging loop antenna applied to an implantable cardiac pacemaker according to the present case.

As shown in FIG. 5, the intracorporal planar loop antenna 2 is placed in a local human body model 3 which is 5 mm deep from a body surface, including a thickness of 2 mm of a skin 4, a thickness of 2 mm of a fat 5, and a thickness of 1 mm of a muscle 6. A dielectric constant of the skin 4 is 46.7, a dielectric constant of the fat 5 is 11.6 and a dielectric constant of the muscle 6 is 57.1. A conductivity of the skin 4 is 0.689 S/m, a conductivity of the fat 5 is 0.0808 S/m and a conductivity of the muscle 6 is 0.797 S/m. The human body model has a length of 100 mm, a width of 100 mm and a height of 15 mm. The extracorporal planar loop antenna 1 is 1 mm away from the body surface, and thus a total distance d from the extracorporal planar loop antenna 1 to the intracorporal planar loop antenna 2 is 6 mm. The extracorporal planar loop antenna 1 converts electric energy into field energy and transmits the field energy to the intracorporal planar loop antenna 2 through magnetic coupled resonance, and the intracorporal planar loop antenna 2 converts the received field energy into the electric energy to complete the process of wireless energy transmission, thereby supplying power to the implantable cardiac pacemaker. Computer simulation technology (CST) software is used for testing and analyzing, and an obtained return loss curve of the extracorporal planar loop antenna 1 is shown in FIG. 6. It can be obtained from the figure that in a case where a center frequency is 403 MHz, the return loss $|S11|=-20.8$ dB, the return loss $|S22|=-22.2$ dB, and the transmission coefficient $|S21|=-2.27$ dB. According to a transmission coefficient graph, an efficiency curve of wireless energy transmission between the extracorporal planar loop antenna 1 and the intracorporal planar loop antenna 2 can be obtained as shown in FIG. 7. In a case where the center frequency is 403 MHz, the energy transmission efficiency is 59.28%, which can meet the requirements for implantable medical equipment with low power consumption.

TABLE ONE

| Dimension Name | Dimension Number | Dimension/mm | Dimension Name | Dimension Number | Dimension/mm |
|---|---|---|---|---|---|
| Substrate width of the extracorporal planar loop antenna | Lp | 40 | Substrate width of the intracorporal planar loop antenna | Ls | 25.5 |
| Gap of the extracorporal planar loop antenna | $n_P$ | 3.4 | Gap of the intracorporal planar loop antenna | $n_s$ | 4.1 |
| Inner radius of the extracorporal planar loop antenna | Rp | 0.5 | Inner radius of the intracorporal planar loop antenna | Rs | 5.56 |
| Width of the first loop radiation patch | $W_1$ | 2.84 | Outer radius of the intracorporal planar loop antenna | Rw | 10.23 |
| Width of the second loop radiation patch | $W_2$ | 6.04 | Total distance between the extracorporal planar loop antenna and the intracorporal planar loop antenna | d | 6 |
| Width of the third loop radiation patch | $W_3$ | 0.64 | Substrate widths of extracorporal planar loop antenna and the intracorporal planar loop antenna | t | 1.5 |

TABLE ONE-continued

| Dimension Name | Dimension Number | Dimension/mm | Dimension Name | Dimension Number | Dimension/mm |
|---|---|---|---|---|---|
| Width of the fourth loop radiation patch | $W_4$ | 0.6 | Distance between the extracorporal planar loop antenna and the body surface | $d_{gap}$ | 1 |
| Gap between the first loop radiation patch and the second loop radiation patch | gap1 | 2.72 | Skin thickness | $d_{skin}$ | 2 |
| Gap between the second loop radiation patch and the third loop radiation patch | gap2 | 2.35 | Fat thickness | $d_{fat}$ | 2 |
| Gap between the third loop radiation patch and the fourth loop radiation patch | gap3 | 2.02 | Muscle thickness | $d_{muscle}$ | 1 |
| Width of the extracorporal radiation patch gap of the first loop radiation patch | $n_1$ | 0.57 | | | |
| Width of the extracorporal radiation patch gap of the second loop radiation patch | $n_2$ | 0.5 | | | |
| Width of the extracorporal radiation patch gap of the third loop radiation patch | $n_3$ | 0.64 | | | |
| Width of the first pair of connection radiation patches | Con1 | 2.47 | | | |
| Width of the second pair of connection radiation patches | Con2 | 1.91 | | | |
| Width of the third pair of connection radiation patches | Con3 | 1.67 | | | |

The present disclosure has the following advantages.

1. The wireless transmission antenna is designed to be planar and multi-loop to increase the magnetic field induction area and enhance the magnetic field density;

2. The patch capacitor is used so that the resonance frequency is reduced to implement impedance matching, thus improving the energy transmission efficiency.

What is claimed is:

1. A wireless charging loop antenna, applied to an implantable cardiac pacemaker, comprising: an extracorporal planar loop antenna and an intracorporal planar loop antenna, wherein the intracorporal planar loop antenna is disposed inside a body, and the extracorporal planar loop antenna is disposed on a skin outside the body;

the extracorporal planar loop antenna comprises an extracorporal antenna substrate, an extracorporal loop radiation patch, paired connection radiation patches and a patch capacitor; the extracorporal loop radiation patch and the paired connection radiation patches form a circuit; the extracorporal loop radiation patch, the paired connection radiation patches and the patch capacitor are all on a same surface of the extracorporal antenna substrate;

the extracorporal loop radiation patch is provided with at least one extracorporal radiation patch gap; the extracorporal loop radiation patch comprises a first loop radiation patch, a second loop radiation patch, a third loop radiation patch and a fourth loop radiation patch; the second loop radiation patch is disposed outside a ring of the first loop radiation patch, the third loop radiation patch is disposed outside a ring of the second loop radiation patch, and the fourth loop radiation patch is disposed outside a ring of the third loop radiation patch;

the patch capacitor is disposed at one of the at least one extracorporal radiation patch gap; and the paired connection radiation patches comprise: a first pair of connection radiation patches, a second pair of connection radiation patches and a third pair of connection radiation patches; the first pair of connection radiation patches connects the first loop radiation patch to the second loop radiation patch; the second pair of connection radiation patches connects the second loop radiation patch to the third loop radiation patch; and the third pair of connection radiation patches connects the third loop radiation patch to the fourth loop radiation patch.

2. The wireless charging loop antenna of claim 1, wherein the patch capacitor is disposed at an extracorporal radiation patch gap of the first loop radiation patch, or at an extracorporal radiation patch gap of the second loop radiation patch, or at an extracorporal radiation patch gap of the third loop radiation patch, or at an extracorporal radiation patch gap of the fourth loop radiation patch.

3. The wireless charging loop antenna of claim 1, wherein the at least one extracorporal radiation patch gap is disposed at any angle of the extracorporal loop radiation patch.

4. The wireless charging loop antenna of claim 1, wherein an extracorporal feed point points from one end of an extracorporal radiation patch gap of the fourth loop radiation patch to the other end of the extracorporal radiation patch gap of the fourth loop radiation patch.

5. The wireless charging loop antenna of claim 1, wherein the intracorporal planar loop antenna comprises an intracorporal antenna substrate and an intracorporal loop radiation patch; the intracorporal loop radiation patch is disposed on the intracorporal antenna substrate; and the intracorporal loop radiation patch is provided with an intracorporal radiation patch gap.

6. The wireless charging loop antenna of claim 5, wherein the intracorporal radiation patch gap is disposed at any angle of the intracorporal loop radiation patch.

7. The wireless charging loop antenna of claim 5, wherein an intracorporal feed point points from one end of the intracorporal radiation patch gap to the other end of the intracorporal radiation patch gap.

\* \* \* \* \*